(12) United States Patent
Eriksen

(10) Patent No.: US 8,328,739 B2
(45) Date of Patent: Dec. 11, 2012

(54) COIL SYSTEM AND METHOD FOR OBTAINING VOLUMETRIC PHYSIOLOGICAL MEASUREMENTS

(75) Inventor: Morten Eriksen, Oslo (NO)

(73) Assignee: VoluSense AS, Bergen (NO)

( * ) Notice: Subject to any disclaimer, the term of this patent is extended or adjusted under 35 U.S.C. 154(b) by 0 days.

(21) Appl. No.: 13/463,117

(22) Filed: May 3, 2012

(65) Prior Publication Data

US 2012/0220901 A1    Aug. 30, 2012

Related U.S. Application Data

(62) Division of application No. 12/426,358, filed on Apr. 20, 2009, now abandoned.

(51) Int. Cl.
  *A61B 5/103*    (2006.01)
  *A61B 5/117*    (2006.01)
(52) U.S. Cl. ...................................................... 600/587
(58) Field of Classification Search .................. 600/587, 600/595
  See application file for complete search history.

(56) References Cited

U.S. PATENT DOCUMENTS

| | | | |
|---|---|---|---|
| 2,649,573 | A | 12/1953 | Goldberg et al. |
| 2,843,825 | A | 7/1958 | Lush |
| 3,142,796 | A | 7/1964 | Goldberg et al. |
| 3,560,845 | A | 2/1971 | Goldberg et al. |
| 3,731,184 | A | 5/1973 | Goldberg et al. |
| 4,083,002 | A | 4/1978 | Allport |
| 4,258,718 | A | 3/1981 | Goldman |
| 4,308,872 | A | 1/1982 | Watson et al. |
| 4,652,823 | A | 3/1987 | Sutton |
| 4,694,837 | A | 9/1987 | Blakeley et al. |
| 4,991,587 | A | 2/1991 | Blakeley et al. |
| 5,038,785 | A | 8/1991 | Blakeley et al. |
| 5,131,399 | A | 7/1992 | Sciarra |
| 5,394,882 | A | 3/1995 | Mawhinney |
| 5,738,102 | A | 4/1998 | Lemelson |
| 5,749,365 | A | 5/1998 | Magill |
| 5,825,293 | A | 10/1998 | Ahmed et al. |
| 5,882,300 | A | 3/1999 | Malinouskas et al. |
| 5,957,854 | A | 9/1999 | Besson et al. |

(Continued)

FOREIGN PATENT DOCUMENTS

DE    4215901    8/1993

(Continued)

OTHER PUBLICATIONS

English Abstract of DE4215901.

(Continued)

*Primary Examiner* — Jeffrey G Hoekstra
(74) *Attorney, Agent, or Firm* — Mintz Levin Cohn Ferris Glovsky and Popeo, P.C.

(57) ABSTRACT

A coil device is provided having a member adapted to extend around and conform to an outer surface of a subject and a conductor adapted to extend only once around a first portion of the subject. The coil device cats be positioned about the subject in order to measure a volume of the subject. When placed about the subject in the presence of a relatively homogeneous magnetic field, the conductor can generate a signal indicative of a volume of the first portion of the subject. The coil device may also include two or more conductors separately generating signals indicating volumes of two or more corresponding portions of the subject. In sonic cases the coil device includes associated authorization data that can limit use of the coil device. Systems and methods incorporating the coil device are also provided.

24 Claims, 13 Drawing Sheets

U.S. PATENT DOCUMENTS

| | | | |
|---|---|---|---|
| 5,964,720 | A | 10/1999 | Pelz |
| 6,106,481 | A | 8/2000 | Cohen |
| 6,374,667 | B1 | 4/2002 | Eriksen et al. |
| 6,434,411 | B1 | 8/2002 | Duret |
| 6,436,053 | B1 | 8/2002 | Knapp et al. |
| 6,480,111 | B2 | 11/2002 | Canady et al. |
| 6,740,046 | B2 | 5/2004 | Knapp et al. |
| 6,945,941 | B2 | 9/2005 | Eriksen et al. |
| 7,390,307 | B2 | 6/2008 | Eriksen et al. |
| 2002/0115925 | A1 | 8/2002 | Avrin et al. |
| 2008/0270067 | A1 | 10/2008 | Eriksen et al. |

FOREIGN PATENT DOCUMENTS

| | | |
|---|---|---|
| GB | 1596298 | 8/1981 |
| GB | 2116725 | 9/1983 |
| JP | 53126786 | 11/1978 |
| WO | WO 9013259 | 11/1990 |

OTHER PUBLICATIONS

European Search Report for European Application No. 09152262.3, dated Mar. 9, 2009.

Office Action for European Application No. 04787568.7, dated Aug. 4, 2006.

Office Action for European Application No. 04787568.7, dated Jan. 19, 2007.

Office Action for European Application No. 09152262.3, dated Nov. 24, 2009.

Mosher et al., "Fetal Magnetocardiography: Methods for Rapid Data Reduction," Review of Scientific Instruments, Amer. Inst. Phys. 68:3, 1587-1595 (1997).

Response to Office Action for European Application No. 09152262.3, dated May 21, 2010.

Response to Office Action for European Application No. 04787568.7, dated Dec. 1, 2006.

Response to Office Action for European Application No. 04787568.7, dated Jul. 17, 2007.

Ripka et al., "Fluxgate Sensor for Magnetopneumometry," Sensors and Actuators A, Elsevier Sequoia S.A., 60:1-3, 76-79 (1997).

Tavrin et al., "A Second-Order Squid Gradiometer Operating at 77 K," Superconductor Science and Technology, IOP Publishing, Techno House, Bristol GB, 7:5, 265-268 (1994).

TTI: "Products," Tristan Technologies, Inc., HTTP://web.archive.org/web/20021205005908/HTTP://tristantech.com/prod_biomagnet.html, XP002332664, pp. 1-11 (2002).

COIL SYSTEM AND METHOD FOR OBTAINING VOLUMETRIC PHYSIOLOGICAL MEASUREMENTS

CROSS REFERENCE TO RELATED APPLICATION

This is a divisional of and claims the benefit of priority from U.S. patent application Ser. No. 12/426,358, filed Apr. 20, 2009, which is hereby incorporated by reference herein in its entirety.

BACKGROUND

Many applications exist in which the accurate measurement of one or more dynamic volumes is desirable. For example, in the field of physiology, medical doctors, researchers and others use volumetric measurements to monitor and characterize physiological functions within a subject (e.g., a human patient), and diagnose ailments thereof.

One specific example includes the measuring of breathing volumes in patients. Respiratory disease is a common and significant problem in both the United States and throughout the world. Obstructions can stem from the constriction of the airways caused by inflammation and edema of the walls of the terminal bronchi, or narrowing of the trachea or the throat. Obstructions in the distal airways generally make expiration slower and/or more difficult as more air is exhaled from the lungs or during the latter part of expiration, while upper airway obstruction might provide a more constant resistance to air flow. Types of respiratory disease include diseases of the lung, bronchial tubes, pleural cavity, upper respiratory tract, trachea, and of the nerves and muscles of breathing. An important step in monitoring for and managing such diseases, as well as less severe respiratory conditions, involves measuring air flow volumes moving into and out of the patient's lungs.

Recording breathing volumes is commonly performed through the use of a volume flow-sensing device connected to a subject's airway (e.g., a spirometer or tachymeter), although such devices can be overly intrusive. Another method for measuring breathing volumes includes measuring the movements of the subject's chest and abdominal walls. These techniques are often strain gauge based (i.e., determining changes in body circumference) or based on elastic inductive electrical conductor loops arranged around the chest and abdomen of the subject. Changes in body circumference, or recordings of the inductance of the loops, can then be used to estimate the magnitude of cross sectional area and volume variations of the chest and abdominal compartments.

The strain gauge or circumferential distance methods have no simple or reproducible relation between the measured variations and the volumes that are measured. This relation depends on assumptions about the relation between the area enclosed by the loop and the length of the loop that are valid only for a fixed geometry. Although some of the methods based on inductance may claim that area is measured (i.e., it is assumed to be proportional to loop inductance), the assumption is only valid as long as the relative shape of the loop is conserved. Unfortunately, this is not the case for the cross-sectional area variations of, e.g., the human chest or abdomen that occur during respiration.

In response to these and other drawbacks of past methods of measuring volumes, VoluSense, the assignee of the present invention, has developed new systems and methods for measuring volumes, including the use of a volume-sensing element and associated electromagnetic induction techniques. Some of these systems and methods are disclosed in VoluSense's U.S. Pat. Nos. 6,374,667; 6,945,941; and 7,390,307, the contents of which are hereby incorporated by reference herein in their entirety.

The electromagnetic induction techniques described in these patents provide a measurable advance over past methods of measuring volumes. However, VoluSense continuously looks for ways to optimize equipment, methods, and other aspects of its existing systems, as will become apparent throughout the remainder of this disclosure.

SUMMARY

Embodiments of the invention relate to devices, systems and methods for measuring static and dynamic volumes, such as, for example, a volume of a subject's abdomen and/or chest. Embodiments of the invention provide simplified and improved techniques that employ a single conductor extending only once around a subject to measure a volume of the subject within a relatively homogeneous magnetic field. Some embodiments of the invention also provide a common area on a coil device where multiple conductors can exit the coil device, thus providing a coil device that can be easily wrapped about a subject to measure a volume. In addition, some embodiments of the invention provide an advantageous use of authorization data that can limit or otherwise control use of a particular coil device.

In some embodiments, a coil device is provided that can be positioned about the subject (e.g., a patient) in order to measure one or more volumes of the subject. The coil device includes a first member adapted to extend around and conform to an outer surface of a first portion of the subject despite changes in a contour of the outer surface. The first member can include a first conductor that is adapted to extend only once around the first portion of the subject. In some cases, the first conductor is adapted to generate a signal indicative of a volume of the first portion of the subject in the presence of a relatively homogeneous magnetic field such as that produced by an electromagnet energized with an alternating current.

In some embodiments, a coil device is provided that includes a first member adapted to extend around an outer surface of a first portion of a subject. The first member includes a first conforming means that conforms the first member to the outer surface of the first portion. The first member also includes a first conducting means. The conducting means can generate, in the presence of a relatively homogeneous magnetic field, a signal indicative of a volume of the first portion of the subject. In some cases, the first conducting means comprises a single conductor adapted to extend only once around the first portion of the subject.

According to another aspect of the invention, a method for measuring a volume of a subject is described. The method includes providing a coil device with a first member having a first conductor and extending the first member around an outer surface of a first portion of the subject. The first member conforms to the outer surface despite changes in a contour of the outer surface. Further, in some cases, the method includes extending the first conductor only once around the first portion of the subject. A relatively homogeneous magnetic field is generated within a predefined spatial volume and the first portion of the subject is positioned within the spatial volume. After positioning the subject and generating the magnetic field, the method includes measuring a signal induced in the first conductor by the magnetic field and estimating a volume of the first portion of the subject based on the measured signal.

In some embodiments, the coil device includes an electronic memory storing authorization data, and the method further includes reading the authorization data from the electronic memory and determining from the authorization data whether use of the coil device is authorized. If use of the coil device is authorized, the method may further include estimating a volume of the first portion of the subject based on a signal induced in the first conductor.

According to another aspect of the invention, in some embodiments, a system for measuring a volume of a subject is provided. The system includes an electromagnet able to generate a relatively homogeneous magnetic field and a coil device having an electronic memory storing authorization data. In some cases the coil device is adapted to conform to an outer surface of a first portion of the subject and generate a signal indicative of a volume of the first portion of the subject in the presence of the relatively homogeneous magnetic field. The system further includes a control system electrically coupled to the coil device. The control system is adapted to read the authorization data from the electronic memory, determine from the authorization data whether use of the coil device is authorized, measure the signal generated by the first conductor, and estimate the volume of the first portion of the subject based on the signal received from the first conductor if use of the coil device is authorized.

Embodiments of the invention provide a number of advantages over conventional devices and methods for measuring a volume of a subject. For example, embodiments of the invention provide a simplified coil device capable of measuring a volume of a subject with a single conductor that only extends once around the subject. This simplified design can be easier and cheaper to manufacture than existing coil devices that measure volume with multiple conductors or multiple turns of a single conductor. In addition, in some embodiments a coil device can be easily wrapped around a subject and coupled to a measuring system due to the lack of multiple conductors or turns and connections associated with past coil devices. In some cases, a coil device is provided with a return conductor that allows all electrical connections to the coil device to be collected in one common area before exiting the coil device. Such a configuration can also aid in placing a coil device about a subject and/or removing it with ease. Some embodiments of the invention provide a number of advantages associated with the use of authorization data. In some cases authorization data associated with a particular coil device can be used to determine whether use of the coil device is authorized. For example, use of a particular coil device may be limited to a predefined number of uses or to an individual patient. Thus, use of the coil device can be limited for a variety of reasons. As just some examples, use may be limited due to sanitation concerns or wear on the coil device, or alternatively, for consistency with a particular business model.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION OF THE PREFERRED EMBODIMENTS

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
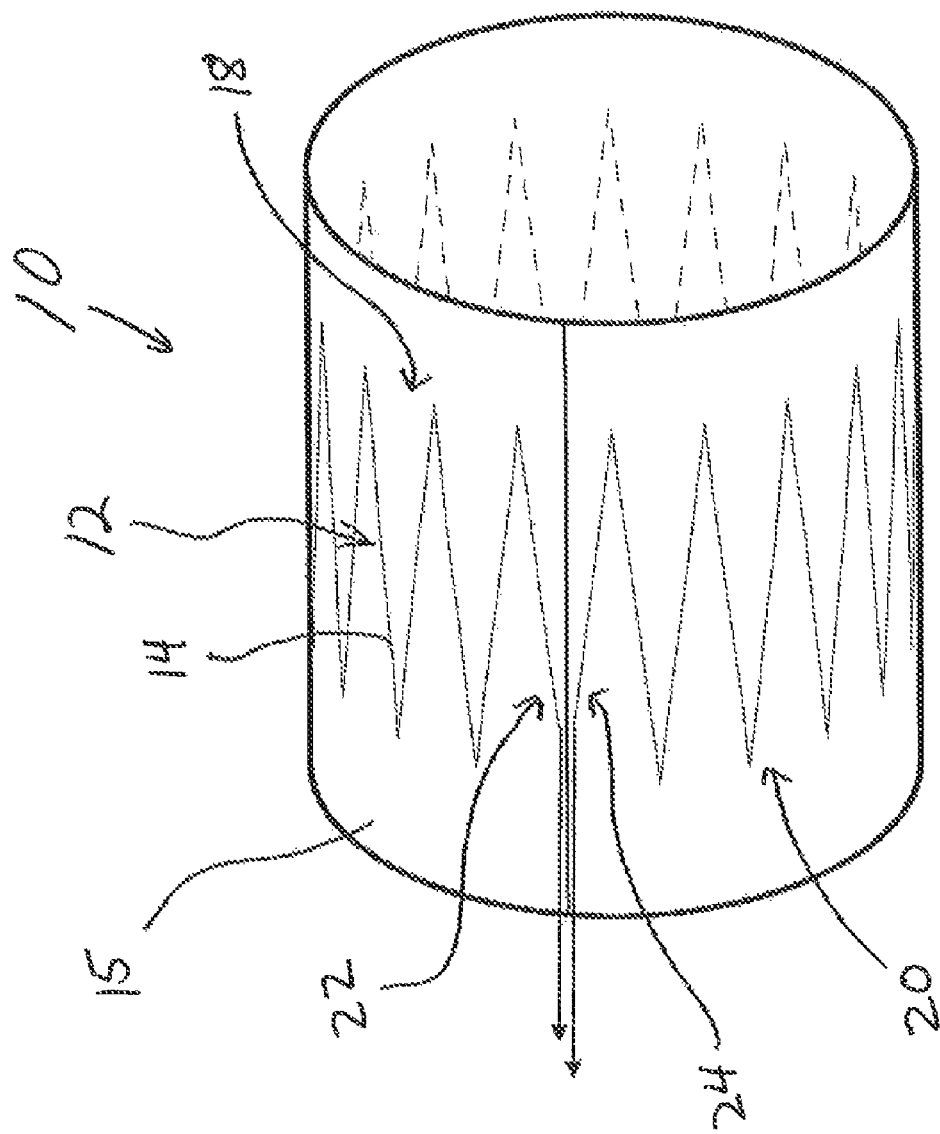
FIG. 1 is a perspective view of a coil device formed into a shape for measuring a volume of a subject according to an embodiment of the invention.

FIG. 1 is a perspective view of a coil device 10 useful for measuring volume with electromagnetic induction techniques according to an embodiment of the invention. The coil device 10 includes a first member 12 that is adapted to extend around an object (e.g., a patient) having a volume to be measured. The first member 12 comprises a configuration of a first conductor 14 that extends around the object. In some embodiments, the first member 12 is carried by a substrate 15 useful for securing the first member 12 about the object. In use, when the coil device 10 and object are placed within a magnetic field, the coil device 10 generates a signal corresponding to a volume of the object. For example, a relatively homogeneous magnetic field can induce a signal in the first conductor that indicates the volume of the object. The induced signal can then be measured to determine the volume. As used herein, the phrases "measuring volume" and "measure a volume" encompass both the concept of quantifying a physical signal directly signifying a volume, as well as quantifying a signal and then calculating, estimating, or otherwise determining a volume based on the quantified signal.

Figure 2:
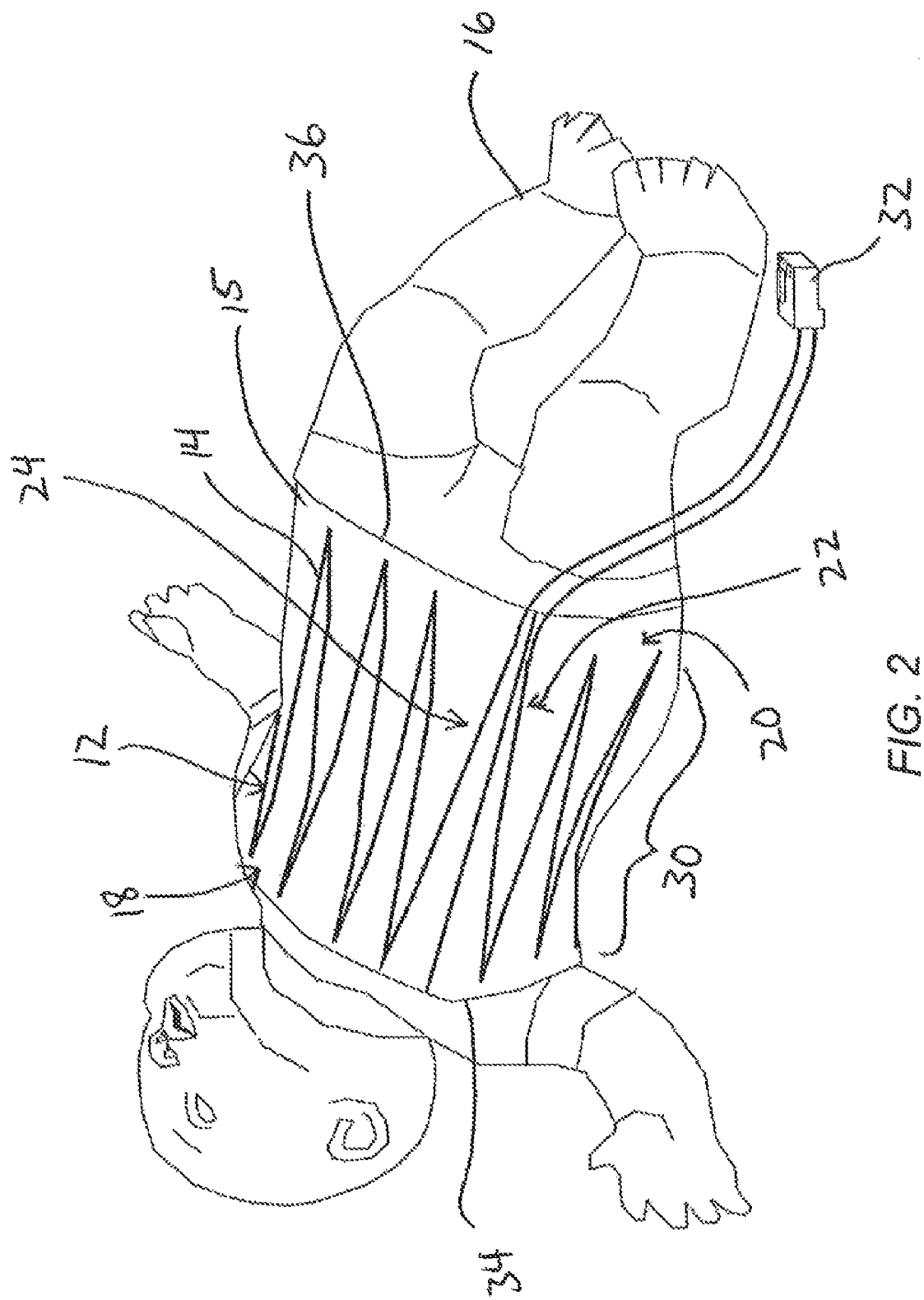
FIG. 2 is a perspective view of the coil device of FIG. 1 placed around a subject according to an embodiment of the invention.

The coil device 10 can be useful for measuring volumes of a variety of objects, including those with irregularly-shaped volumes and/or volumes that change over time. In some cases, the coil device 10 can be useful for measuring changes in volume. For example, as shown in FIG. 2, the coil device 10 can be placed about the chest and/or abdomen of a subject 16 to measure a breathing volume, or a change in the breathing volume, of the subject 16. In additional embodiments, the coil device 10 includes an electronic memory (not shown in FIG. 1 or 2) storing authorization data. As will be described in more detail, the authorization data can provide a secure environment and ensure that only authorized uses of the coil device 10 are allowed. For example, each coil device may be limited to a specified subject or number of uses.

Embodiments of the coil device 10 can be especially useful for measuring breathing volumes of human subjects, including fully grown adults, adolescents, and, as shown in FIG. 2, infants. Such volume measurements can aid in characterizing respiratory conditions and diagnosing respiratory diseases, but can also be helpful in a wide variety of applications, including, but not limited to physiological research. In addition, while embodiments of the invention are discussed herein with reference to human subjects, the embodied devices, systems, and methods are equally applicable to non-human subjects.

Returning to FIGS. 1 and 2, the first member 12 of the coil device 10 includes a configuration of the first conductor 14 extending around the volume to be measured. In some embodiments the configuration of the first conductor 14 defines a first edge 18 and an opposed, second edge 20 of the first member 12. For example, referring to FIG. 2, the first member 12 may be positioned about the subject 16 so that the first member's first edge 18 is nearer the subject's head, while the second edge 20 is nearer the subject's feet. A distance between the first edge 18 and the second edge 20 can be considered the width of the first member 12.

In some embodiments, the configuration of the first conductor 14 also defines a first end section 22 and an opposed second end section 24 of the first member 12. Referring to FIG. 2, the first end section 22 is positioned proximate to the opposed second end section 24 as the first member 12 wraps around the subject 16. Thus the first conductor 14 also extends about the subject. In some cases the first member 12 may fully wrap around the subject's torso so that its first and second end sections 22, 24 are positioned closely adjacent each other as shown in FIGS. 1 and 2, while in other cases, the first and second end sections 22, 24 may be separated by some amount, so that the first member 12 extends less than completely about the subject 16. A distance between the first and second end sections 22, 24 can be considered the length of the first member 12.

Figure 3:
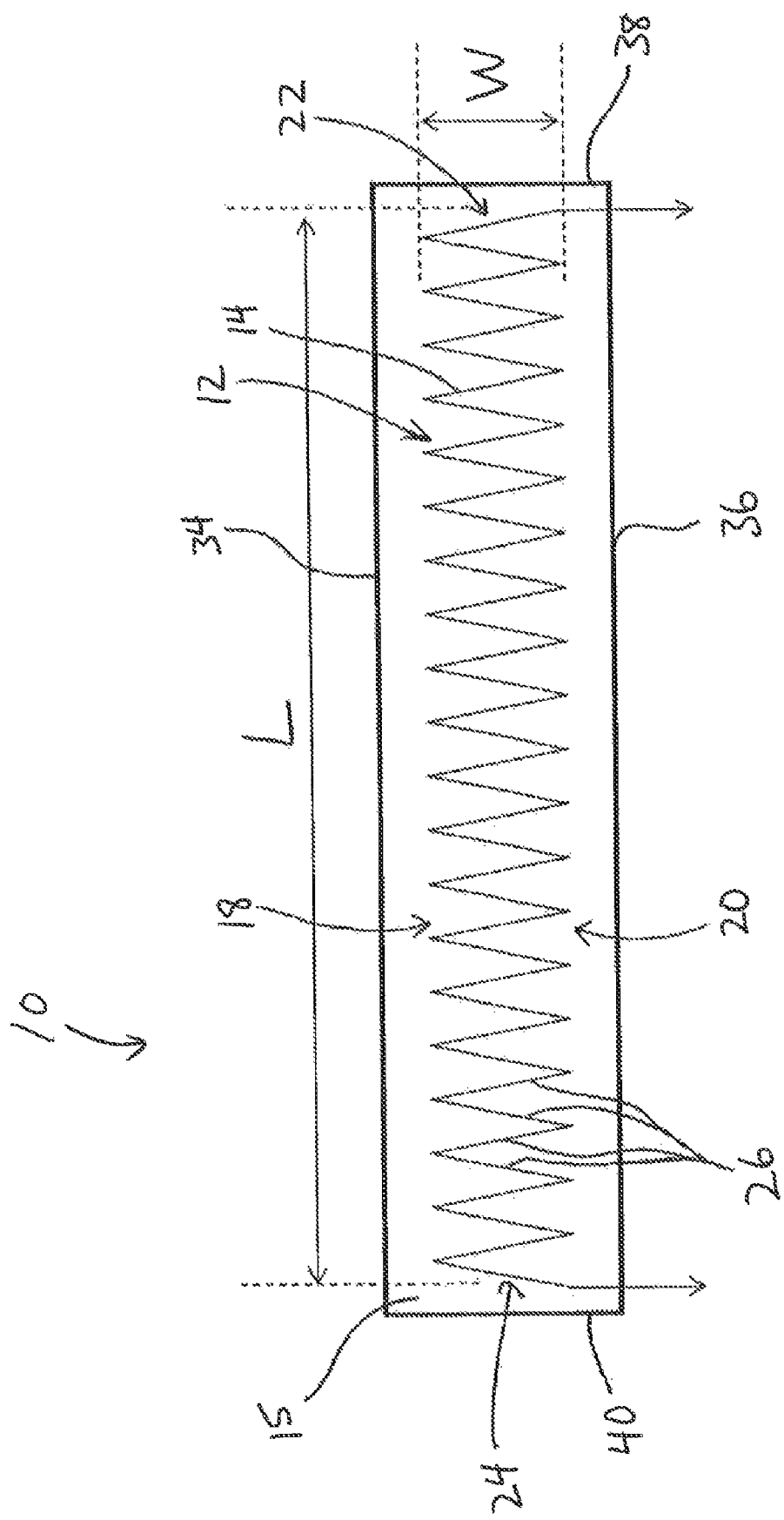
FIG. 3 is a top view of the coil device of FIG. 1 spread out and laid flat.

In some embodiments, the first member 12 (and any optional substrate 15) can have a planar configuration that is wrapped about the subject 16 to measure volume. FIG. 3 illustrates a top planar view of the coil device 10 spread out and laid flat when not wrapped around the subject 16. FIG. 3 illustrates the opposed edges 18, 20 of the first member 12 and the opposed end sections 22, 24 according to one embodiment. In some embodiments, the first conductor 14 is configured to include a number of angled segments 26 extending substantially between the first and second opposed edges 18, 20 at multiple points. For example, the angled segments 26 may form the first conductor 14 in a zigzag pattern or configuration. The angled segments 26 are preferably straight, of substantially the same length and formed at identical, symmetrical angles, although these may not be necessary. For example, in some embodiments the angled segments 26 may have varying lengths and/or angles such that the width W of the first member 12 varies along its length L.

In one embodiment, the first conductor 14 includes at least thirty angled segments 26. In some such embodiments, the first conductor 14 crosses back and forth at least fifteen times from the first end section 22 to the second opposed end section 24. The number of angled segments 26 may vary depending upon a variety of factors including the size of the subject and the measurement accuracy desired. For example, the number of angled segments 26 may be less or more than thirty. In some cases, the strength of the correlation between the induced signal and the volume of the subject 16 to be measured increases as the number of angled segments 26 between the first and second opposed end sections 22, 24 increases.

Returning to FIG. 2, in some embodiments the first member 12 is adapted to extend around an outer surface of a first portion 30 of the subject's abdomen and/or chest. For example, the width of the first member 12 may be great enough to cover substantially all of the subject's abdomen and chest, as shown in FIG. 2. In other cases, the first member 12 may only extend around all or only a portion of the subject's abdomen or all or only a portion of the subject's chest. Those skilled in the art will appreciate that a variety of configurations are possible, and may include configurations for other portions of the subject's body as well.

The first member 12 can conform to the outer surface of the first portion despite changes in the contour of the outer surface. Such contour changes can result in a varying cross-sectional area of the first portion 30 between the first and second edges of the first member. For example, the outer surface of the first portion 30 may be formed in a somewhat variable and irregular shape, and include the natural contours of the subject's torso, e.g., widening at the hips and chest. In addition, the contour of the subject's outer surface may change while the subject 16 breathes and the subject's chest and/or abdomen rise and fall. Accordingly, in some embodiments movement of the first member is representative of movement of the underlying portion of the subject 16.

According to some embodiments of the invention, when the subject 16 and the coil device 10 are placed within a relatively homogeneous, time-varying magnetic field, the first conductor 14 generates a signal indicative of a volume of the first portion 30 of the subject 16. The first conductor 14 can in some cases be considered the magnetic equivalent of a single, planar loop having a cross-sectional area equal to the average cross-sectional area of the first portion 30. In this embodiment the first conductor 14 generates a signal corresponding to the average cross-sectional area of the first portion 30. This signal can then in turn be used to measure the volume of the first portion 30 of the subject 16.

In some cases the induced signal (e.g., a voltage) is related to the volume of the first portion 30 by a proportionality constant. For example, the signal generated by the first conductor 14 may be proportional to the volume of the first portion 30 by an approximate proportionality constant equal to the width W of the first member 12 (i.e., the distance between the first and second opposed edges 18, 20 of the first member). Thus, in some embodiments, the induced signal is related to the configuration of the first conductor's angled segments 26.

As will be appreciated from the discussion and figures herein, embodiments of the invention are useful for measuring volumes with a single turn or winding of a single conductor. Referring to FIG. 2, according to some embodiments the first conductor 14 extends only once around the first portion 30 of the subject of the coil device 10. An electrical connector 32 coupled with the ends of the first conductor 14 can provide a convenient manner for coupling the coil device 10 with measuring equipment. Thus embodiments of the coil device 10 include a simpler configuration for measuring or estimating volumes, especially when compared to devices with multiple windings of a single conductor, or single turns of multiple conductors.

As shown in FIG. 2, in some embodiments the first member 12 conforms to the outer surface of the first portion 30 of the subject 16. In some cases the optional substrate 15 assists the first member 12 in conforming to the outer surface of the first portion 30. In other embodiments, the first member 12 can have inherent material properties that assist in conforming to the outer surface of the first portion 30.

For example, the first member 12 can itself have stretchable properties that provide a close, conforming fit around the subject 16 without the use of a separate substrate. In some cases the first member 12 may be manufactured from a material with an inherent spring constant or other elastic properties. In another embodiment, the angled segments 26 of the first member 12 may stretch apart at their common joints, thus increasing the angles between adjacent segments 26 and stretching the first member 12 to the necessary degree to extend around and conform to the outer surface of the first portion 30 of the subject 16.

Referring to FIGS. 1-3, in another embodiment, the coil device 10 can include the substrate 15 that carries the first member 12 and ensures that the first member 12 conforms to the subject. In some embodiments the substrate 15 has elastic or other stretchable qualities, similar in some cases to spandex or rubber. The first conductor 14 may be fastened to the substrate in a variety of manners, including using plastic welding, glue, stitching, or any other means known in the art. In some cases, the first conductor 14 may be fastened by incorporating it into the substrate during the weaving or manufacture of the substrate.

Figure 4:
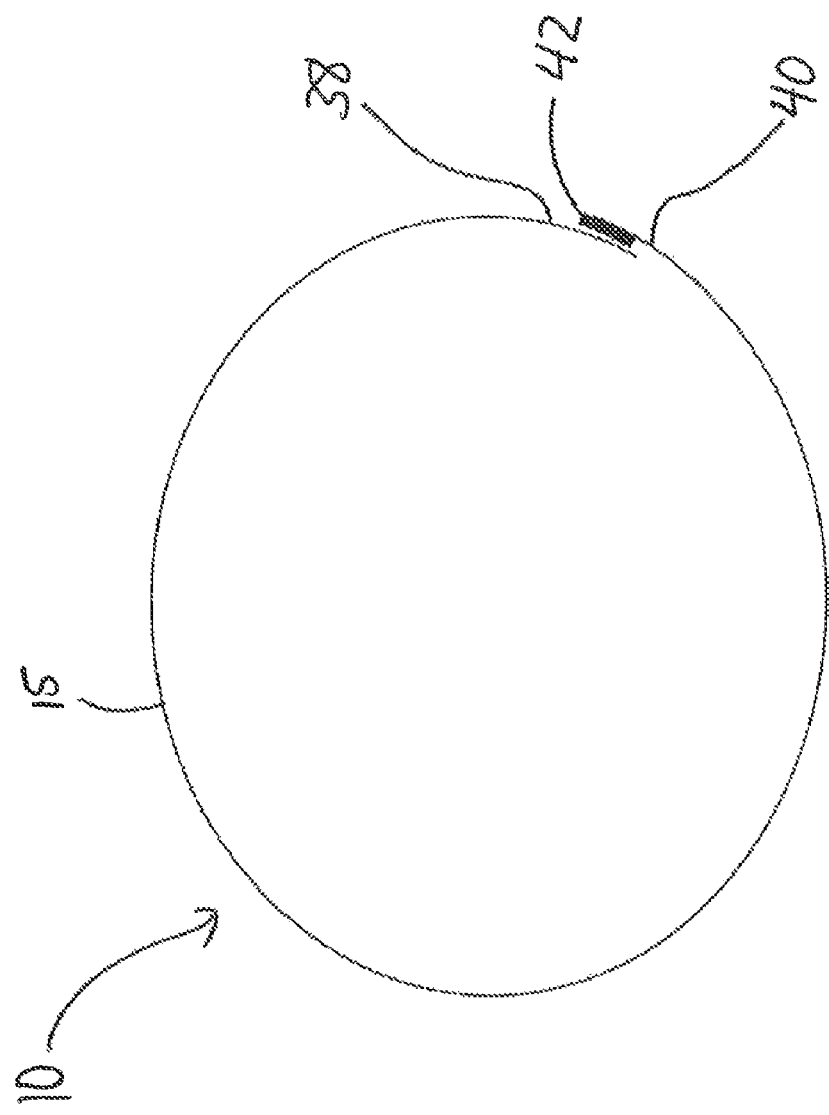
FIG. 4 is a side view of the coil device of FIG. 1.

In some embodiments, the substrate 15 can take the form of a planar sheet that can be wrapped about the first portion 30 of the subject 16. For example, referring to FIGS. 2 and 3, the substrate 15 may have a first edge 34 and an opposing second edge 36, with the first edge 34 nearer the subject's head and the second edge 36 nearer the subject's feet. As shown in FIG. 3, the substrate 15 can also include a first end section 38 and an opposing second end section 40. As shown in FIGS. 3 and 4, the first and second end sections 38, 40 of the substrate 15 (as well as the first and second end sections, 22, 24 of the first member) are adapted to be positioned proximate one another as the substrate 15 and the first member 12 extend around the first portion 30 of the subject.

Once positioned, the first and second end sections can be secured to conform the substrate to the outer surface of the first portion 30. For example, in some cases the first and second end sections 38, 40 of the substrate may be secured directly to the subject 16 with e.g., an adhesive tape. In another embodiment, the substrate 15 includes a fastener 42 for fastening the first end section 38 to the second end section 40. For example, the fastener 42 may include a variety of fasteners, such as hook-and-loop, adhesive, snaps, zippers, buttons, and/or staples.

Referring to FIG. 4, in some embodiments the first and second end sections 38, 40 of the substrate 15 can be secured in a number of positions to provide an adjustable substrate able to accommodate differently sized subjects. For example, in one case the substrate's first end section 38 can be secured at multiple points along the interior surface of the substrate's second end section 40, providing an increasingly snug fit. In some embodiments any unused "flap" of the substrate 15 at the second end section 40 may be tucked underneath the subject 16 such that it is less likely to move as the subject 16 breathes. This may increase the signal accuracy of the coil device 10.

While the substrate 15 is shown in FIGS. 1-4 as a planar body that may be wrapped about the subject 16, other configurations are possible and the invention is not limited to any single configuration. For example, in some embodiments, the substrate 15 may be configured in the shape of a continuous sleeve or other similar shape that can be positioned about the subject 16 by pulling it over the subject's head or legs.

The substrate 15 comprises a stretchable material such as spandex or rubber, and in some embodiments can be formed from an elastic medical bandage material. In some embodiments, an electrically insulating layer of material is preferably positioned over the substrate 15 and the first conductor 14. The first conductor 14 may comprise any electrically conducting material known in the art. For example, the first conductor may comprise copper. In another embodiment, the first conductor 14 may be stamped or cut from a thin metal foil sheet (e.g., aluminum). In sonic cases this can provide an easily constructed and disposable coil device.

As will be appreciated from the discussion and figures herein, embodiments of the invention are useful for measuring volumes with a single turn or winding of a single conductor. Thus the coil device 10 includes a less complex configuration for measuring a volume of the first portion 30 of the subject 16 when compared to devices with multiple windings of a single conductor, or with single turns of multiple conductors. For example, with only a single conductor rather than multiple conductors, the coil device 10 requires fewer electrical connections that in past designs. Fewer electrical connections can simplify the measurement process by, for example, making the coil device 10 easier to place around and remove from a subject. In addition, the single turn of the first conductor 14 allows a simpler and less expensive production process for manufacturing the coil device 10, especially when compared with devices including multiple conductors for measuring volume.

Figure 5:
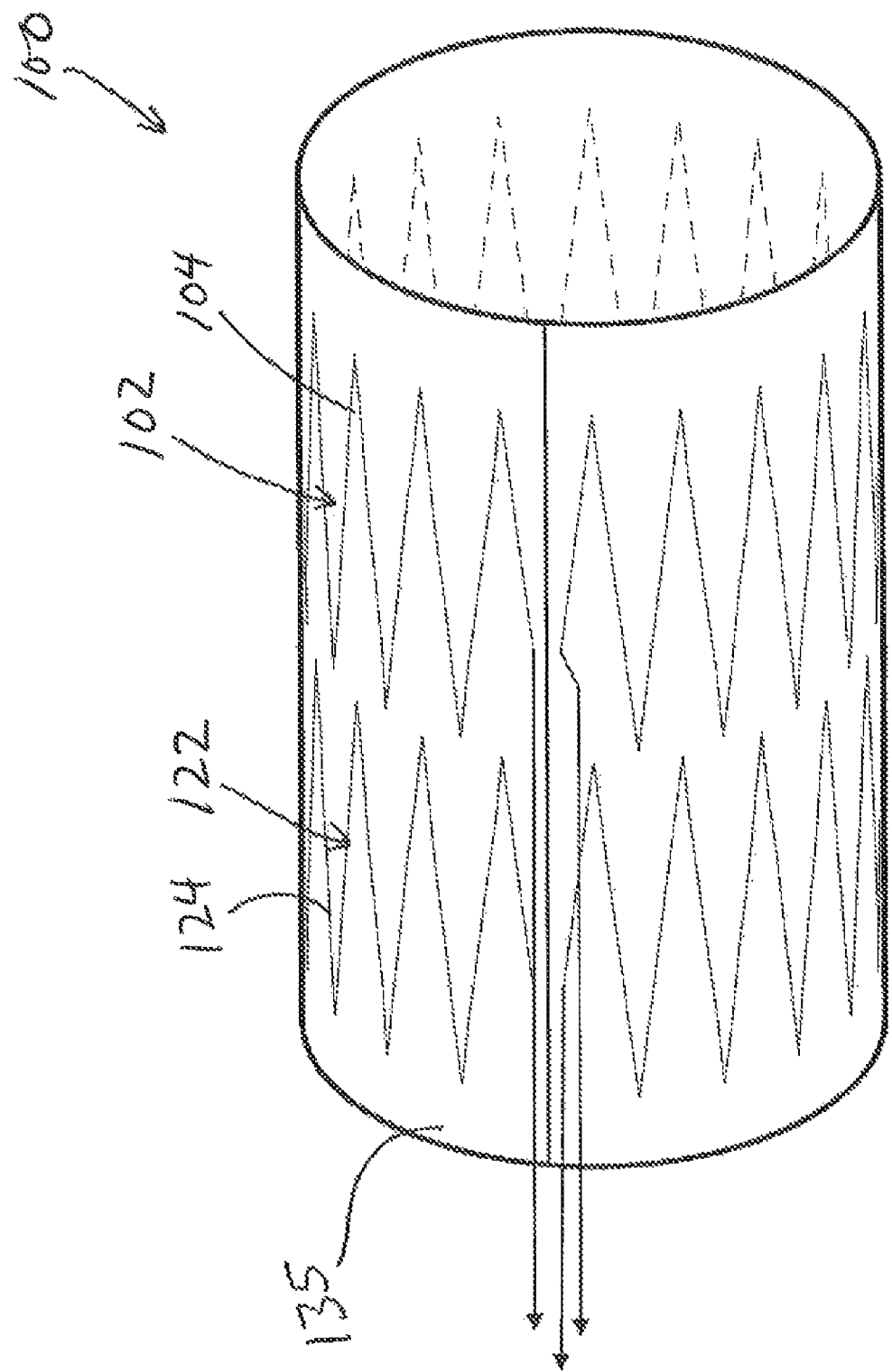
FIG. 5 is a perspective view of a coil device formed into a shape according to another embodiment of the invention.
Figure 6:
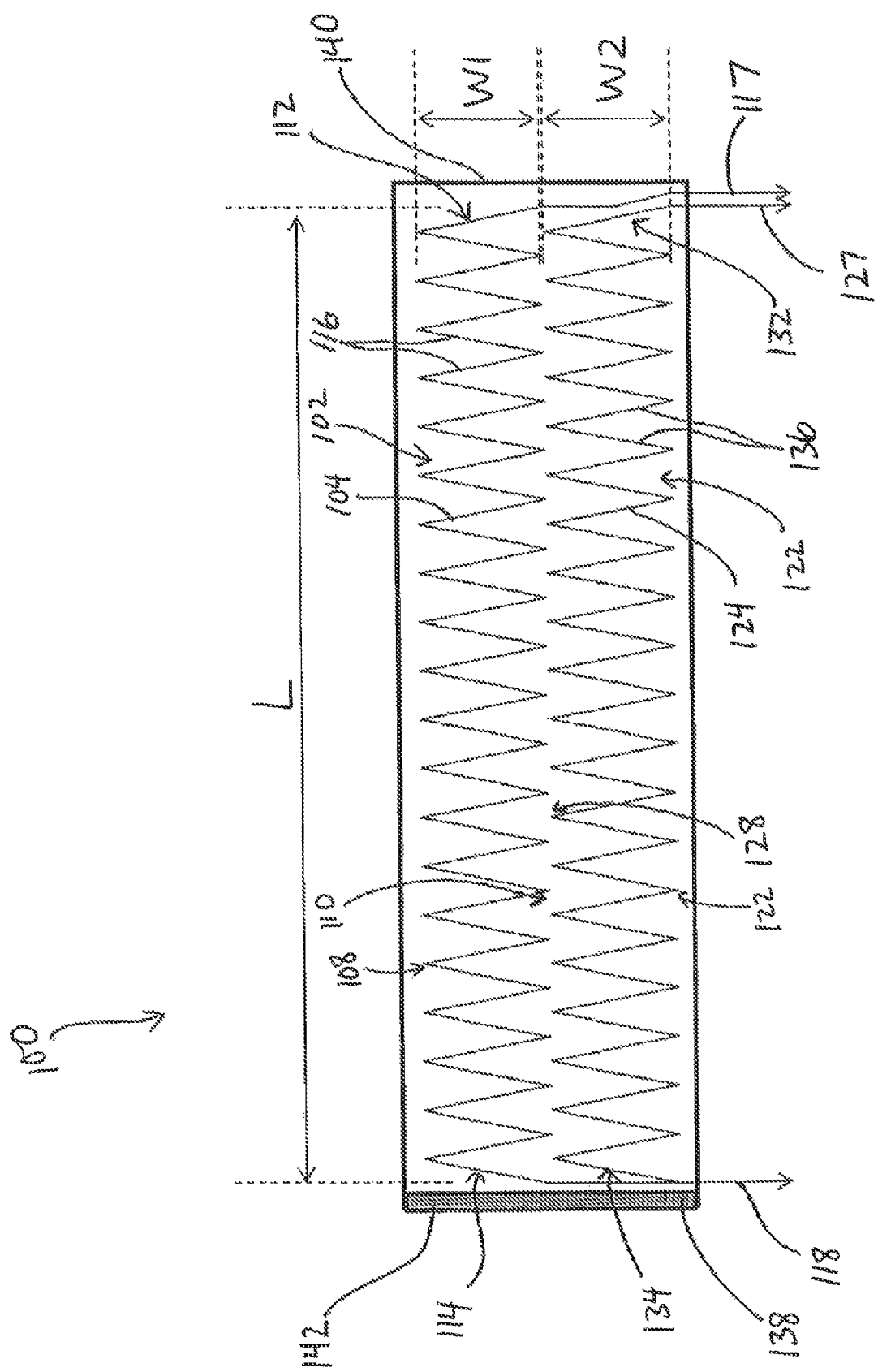
FIG. 6 is a top view of the coil device of FIG. 5 spread out and laid flat.
Figure 7:
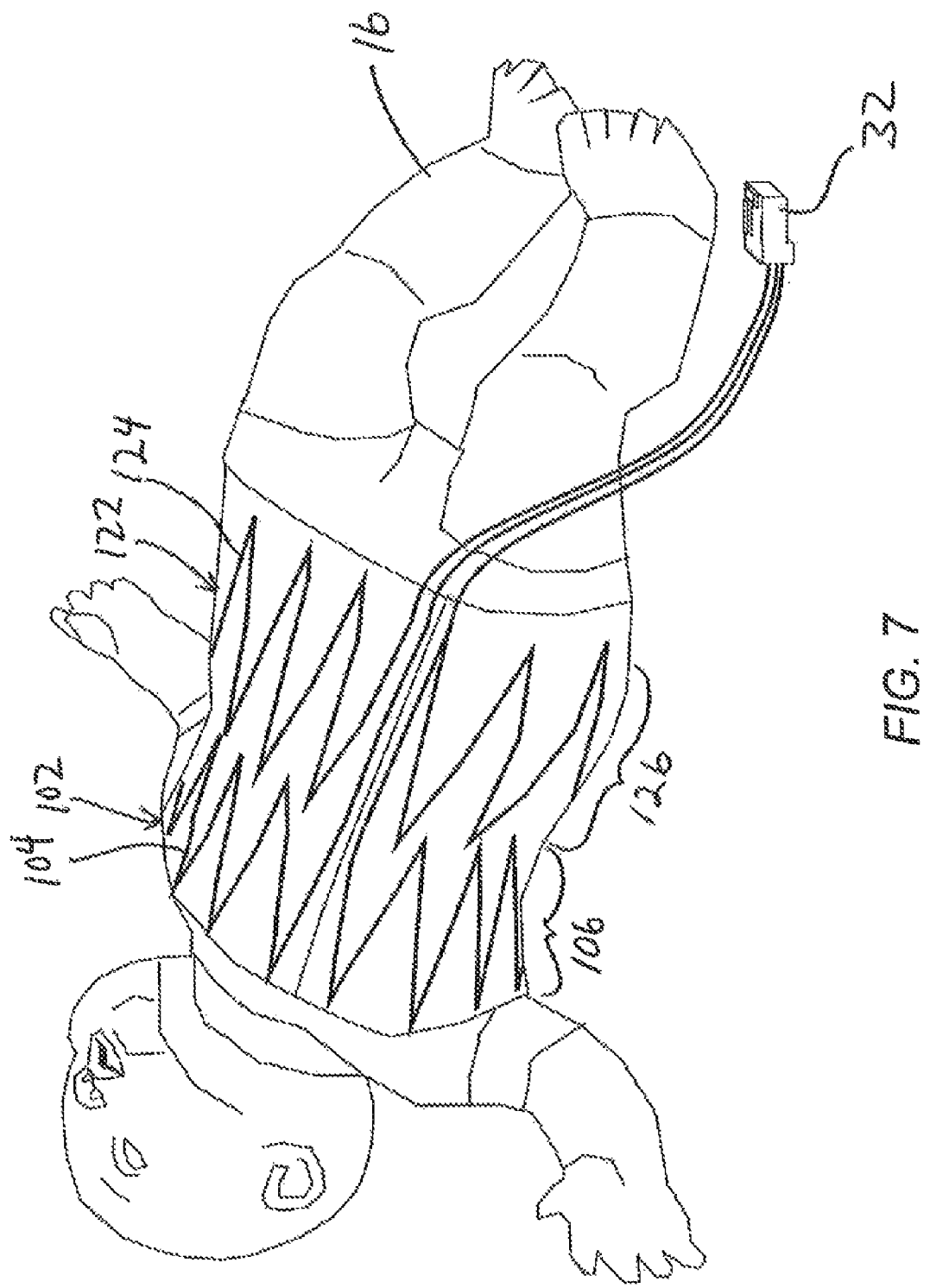
FIG. 7 is a perspective view of the coil device of FIG. 5 placed around a subject according to an embodiment of the invention.

Turning now to FIGS. 5-7, various views are shown of a coil device 100 having multiple conductors for measuring multiple independent volumes of the subject 16. The coil device 100 includes a first member 102 having a first conductor 104 for measuring a volume of a first portion 106 of the subject 16. The coil device 100 further includes a second member 122 with a second conductor 124 for measuring a volume of a second portion 126 of the subject 16. The first and second members 102, 122 advantageously allow independent measurement of two separate volumes. For example, as shown in FIG. 7, in some cases the first member 102 can be positioned around part or all of the subject's chest and the second member 122 can be positioned around part or all of the subject's abdomen. Such a configuration can be useful for detecting when the subject's abdomen moves in asynchrony with the subject's chest indicating an asynchronous breathing pattern. In addition, the volumes of the first and second portions can be summed to estimate the tidal breathing volume of the subject 16.

The first member 102, first conductor 104, second member 122 and second conductor 124 have features similar and generally corresponding to the first member 12 and first conductor 14 of the coil device 10 depicted in FIGS. 1-4. For example, the first member 102 has first and second edges 108, 110 and the second member 122 has first and second edges 128, 130. In addition, the first member 102 has a first end section 112 and a second end section 114, while the second member 122 also includes a first end section 132 and a second end section 134. Each of the first and second conductors 104, 124 includes a number of angled segments 116, 136, respectively, that substantially extend between the respective first and second edges of each member.

According to some embodiments of the invention, when the subject 16 and the coil device 100 are placed within a relatively homogeneous, time-varying magnetic field, the first conductor 104 generates a signal indicative of a volume of the first portion 106 of the subject 16 and the second conductor 124 generates a signal indicative of a volume of the second portion 126 of the subject 16. Each conductor can in some cases be considered the magnetic equivalent of a single, planar loop having a cross-sectional area equal to the average cross-sectional area of the first portion 106 and the second portion 126, respectively. The signals generated correspond to the average cross-sectional areas and can then in turn be used to measure the volumes of the first and second portions 106, 126 of the subject 16.

In some cases the induced signal (e.g., a voltage) in each conductor is related to the measured volume by a proportionality constant. For example, referring to FIG. 6, the signal generated by the first conductor 104 may be proportional to the volume of the first portion 106 by an approximate proportionality constant equal to the width W1 of the first member 102 (i.e., the distance between the first and second opposed edges 108, 110 of the first member). Similarly, the signal generated by the second conductor 124 may be proportional to the volume of the second portion 126 by an approximate proportionality constant equal to the width W2 of the second member 122 (i.e., the distance between the first and second opposed edges 128, 130 of the second member).

The coil device 100 can be coupled with a control system as desired by leads extending from the end sections of the first and second conductors. In some cases each of the first and second conductors 104, 124 may be coupled individually to the larger system or possibly by a shared common return conductor. For example, referring to FIG. 6, in some embodiments the first conductor can be coupled to the larger system by a first lead 117 at the first end section 112 of the first member 102 and a return lead 118 at the second end section 114 of the first member 102. The second conductor can be similarly coupled to the system by a second lead 127 at the first end section 132 of the second member 122 and the same return lead 118 also at the second end section 134 of the second member 122. Referring to FIG. 7, a single connector 32 may couple the leads to the system together, or alternatively, the leads may be individually coupled to the system. Depending upon the desired configuration, the leads 117, 118, and 127 can comprise an integral portion of the one or more of the first and second conductors or may include separate, individual wires coupled to one or more of the first and second conductors.

As with the coil device 10 of FIGS. 1-4, the coil device 100 of FIGS. 5-7 can conform to the outer surface of the first and second portions of the subject despite changes in the contour of the outer surface. In some cases an optional substrate 135 assists the first and second members 102, 122 in conforming to the outer surface. In some embodiments, the first and second members can have inherent material properties that assist in conforming to the outer surface of the subject 16.

For example, the first and second members 102, 122 can themselves have stretchable properties that provide a close, conforming fit around the subject 16 without the use of a separate substrate. In some cases the first and second members may be manufactured from a material with an inherent spring constant or other elastic properties. In another embodiment, the angled segments 116, 136 may stretch apart at their common joints, thus increasing the angles between adjacent segments and stretching the first and second members to the necessary degree to extend around and conform to the outer surface of the first and second portions 106, 126 of the subject 16, respectively.

Referring to FIGS. 5-7, in another embodiment, the coil device 100 includes the single substrate 135 that carries both the first and second members and ensures that the members conform to the subject. In some embodiments the substrate 135 has elastic or other stretchable qualities, similar in some cases to spandex or rubber. The conductors 104, 124 may be fastened to the substrate in a variety of manners, including using plastic welding, glue, stitching, or any other means known in the art.

As shown in FIGS. 5-7, the substrate 135 can in some embodiments take the form of a planar sheet that can be wrapped about the first and second portions 106, 126 of the subject 16. Once positioned, first and second end sections 140, 142 of the substrate can be secured to conform the substrate to the outer surface of the subject 16. For example, in some cases the end sections may be secured directly to the subject 16. In some cases, the substrate 135 includes a fastener 138 for fastening the end sections of the substrate together.

In addition, while the substrate 135 is shown as a planar body that may be wrapped about the subject 16, other configurations are possible and the invention is not limited to any single configuration. For example, in some embodiments, the substrate 135 may be configured in the shape of a continuous sleeve or other similar shape that can be positioned about the subject 16 by pulling it over the subject's head or legs.

As will be appreciated, a wide variety of configurations of the first and second members 102, 122 are possible. For example, in some embodiments of the invention, the first and second members 102, 122 may share the same substrate 135, while in other cases the first member 102 may be carried by a first substrate and the second member 122 may be carried by a second substrate. Also, the first and second members 102, 122 may be positioned adjacent one another, as in FIG. 7, or some gap may be provided between the first and second members according to the desired portions of the subject to be measured. At least in one embodiment, the first member 102 is adapted to extend around at least a portion of the subject's chest, and the second member 122 is adapted to extend around at least a portion of the subject's abdomen.

Figure 8:
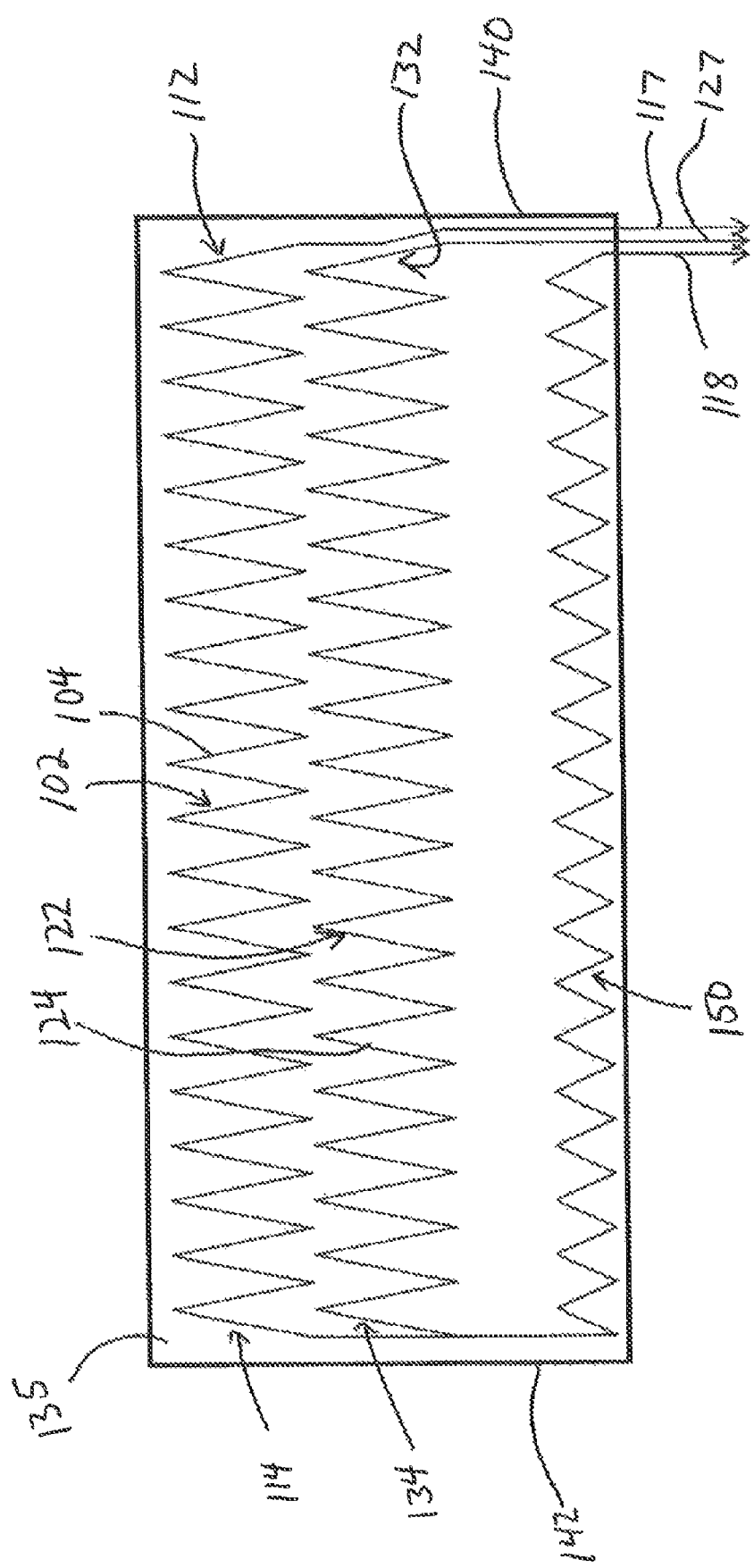
FIG. 8 is a top view of a coil device spread out and laid flat according to another embodiment of the invention.
Figure 9:
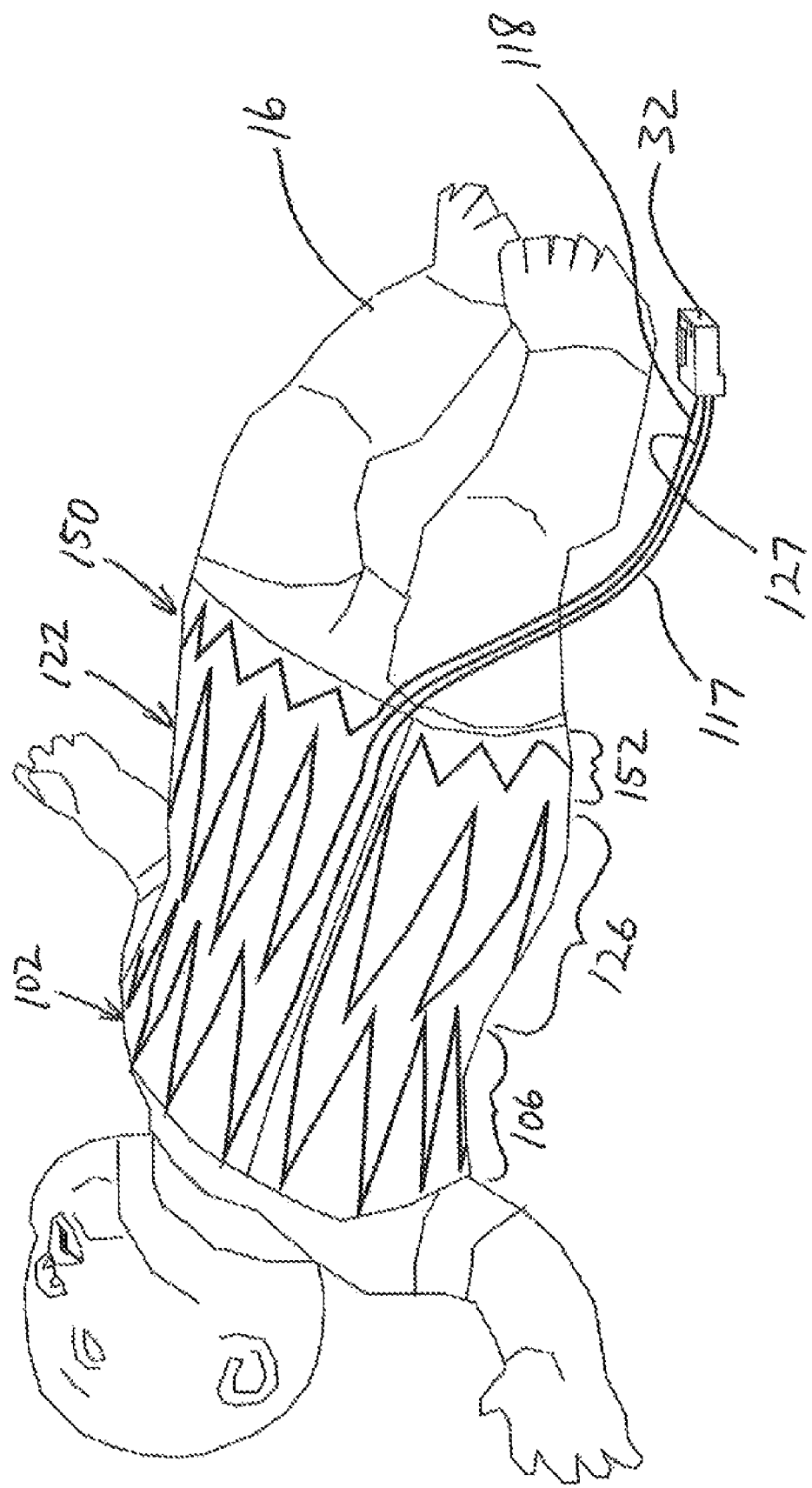
FIG. 9 is a perspective view of the coil device of FIG. 8 placed around a subject according to an embodiment of the invention.

Referring to FIGS. 8-9, in some embodiments a third return conductor 150 is provided for coupling the first and second conductors 104, 124 to a control system. For example, with respect to FIG. 8, the third conductor 150 may be coupled to the first and second conductors 104, 124 proximate the second end section 142 of the substrate 135. The common third conductor 150 then extends back along the substrate 135 towards the first end section 140 of the substrate 135 and is coupled to (or alternatively integral with) the common return lead 118. When using this arrangement, the voltage that is induced in the common third conductor 150 will be subtracted from the voltage induced in the first and second conductors. In some embodiments, the third conductor 150 is located over a body portion that does not change its volume during respiration. This positioning can increase the accuracy of measurements of respiratory variations in the volumes of body portions covered by the first and second conductors.

As shown in FIG. 8, the configuration in this embodiment allows all three conductors to exit the substrate 135 via leads 117, 118, and 127 at a common area proximate the first end section 140 of the substrate 135. Referring to FIG. 9, this configuration provides a simplified wiring scheme with a common coupling point at the connector 32 and allows the coil device 100 to be easily wrapped around the subject 16 without tangling or pulling at leads exiting from opposite end sections of the substrate.

As shown in FIG. 9, in some embodiments the common third conductor 150 is adapted to extend around an outer surface of a third portion 152 of the subject 16. In some cases, the third portion 152 of the subject 16 preferably has a relatively constant volume which does not change during respiration. For example, FIG. 9 depicts the third conductor 150 extending around an area near the hips of the subject 16. Such an arrangement allows the signal induced in the third conductor by the magnetic field to be more easily separated from the desired signals induced in the first and second conductors, thus providing an accurate measurement of the volume variations in body parts covered by the first and second conductors as previously mentioned.

In addition, in some cases the third conductor 150 provides an additional advantage for noise cancellation. As will be appreciated, noise from external sources induces noise signals in the first, second, and third conductors of the coil device 100. Because the third conductor 150 extends around the subject 16 in the opposite direction from the first and second conductors, noise signals originating from external magnetic fields induced in the third conductor 150 will have a polarity opposite of noise signals induced in the first and second conductors. These signals of opposite polarity will have a tendency to cancel each other, and thus some embodiments of the coil device provide enhanced noise performance.

Figure 10:
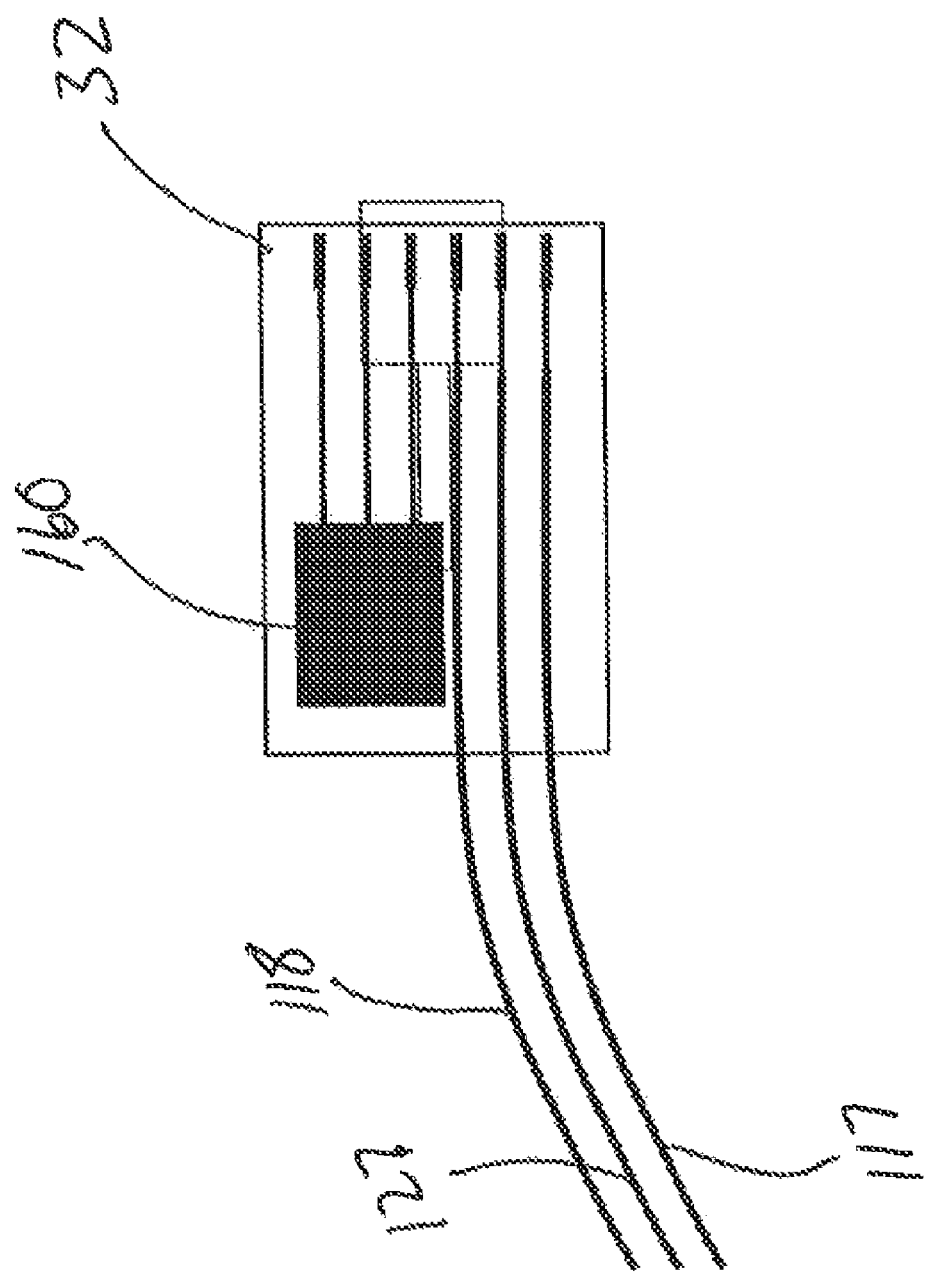
FIG. 10 is a schematic of a coil device connector according to an embodiment of the invention.

In additional embodiments, any of the coil devices 10, 100 can include an electronic memory storing authorization data for determining whether use of the coil device is authorized. Referring now to FIG. 10, in some cases an electronic memory 160 is provided within the connector 32. Any other suitable placement, including on the coil device substrate, can be used depending upon the desired configuration. Placing the electronic memory 160 within the connector 32 can provide a convenient connection point for securing the memory 160 within the coil device while minimizing electrical connections and wire lengths.

The connector 32 can be provided in any number of the wide variety of forms available in the art. In one embodiment, the connector 32 is provided as a 6P6C plug, which conveniently provides three lines for the three leads 117, 118, 127, and three dedicated lines for the electronic memory 160. The memory 160 can be provided in a wide variety of formats and sizes. In some cases the memory 160 is configured as TO-92 package with three leads and with 1024 bits. In at least one embodiment the electronic memory 160 is a programmable read-only memory, which allows the connected control system to write to the memory 160 once and then read it many times.

The authorization data within the electronic memory 160 can comprise a variety of information. In some embodiments the authorization data limits the number of uses of the coil device. For example, the authorization data may include a maximum count corresponding to the maximum number of authorized uses allowed for the coil device. The authorization data may also include a current count that can be compared to the maximum count to determine if use of the coil device is authorized. The authorization data may also include a stored identifier corresponding to a particular subject that may be authorized to use the coil device.

As will be discussed in further detail, the authorization data can be implemented into volume measurement procedures in a variety of ways. For example, when an operator, such as a laboratory technician connects a particular coil device to a control system, the control system can retrieve the authorization data from the coil device and determine if use of the device is authorized. If use is authorized, the operator can then place the coil device around a subject and measure the desired volume. Alternatively, if use is not authorized, the control system can, for example, display an error message and stop the measurement process.

Accordingly, the authorization data can limit use of a particular coil device when desirable. For example, in some embodiments a coil device may be provided in a disposable, single-use form. In this case, it may be desirable to limit the coil device to a single use in accordance with, for example, sanitation policies or business practices, and/or because of ordinary wear and tear on the coil device. The number of authorized uses can be adjusted to any suitable number as desired. Also, it may be desirable to limit use of a reusable coil device to a single subject, again due to, for example, sanitation and/or a particular business model.

In addition to or instead of authorization data, the electronic memory 160 may include a wide variety of other information. For example, in some embodiments the electronic memory 160 stores one or more proportionality constants corresponding to one or more members of the coil device as previously explained. A control system coupled to the coil device can retrieve the proportionality constant(s) from the memory and use them with the induced signal(s) measured from the conductor(s) to estimate the one or more volumes of the subject.

Figure 11:
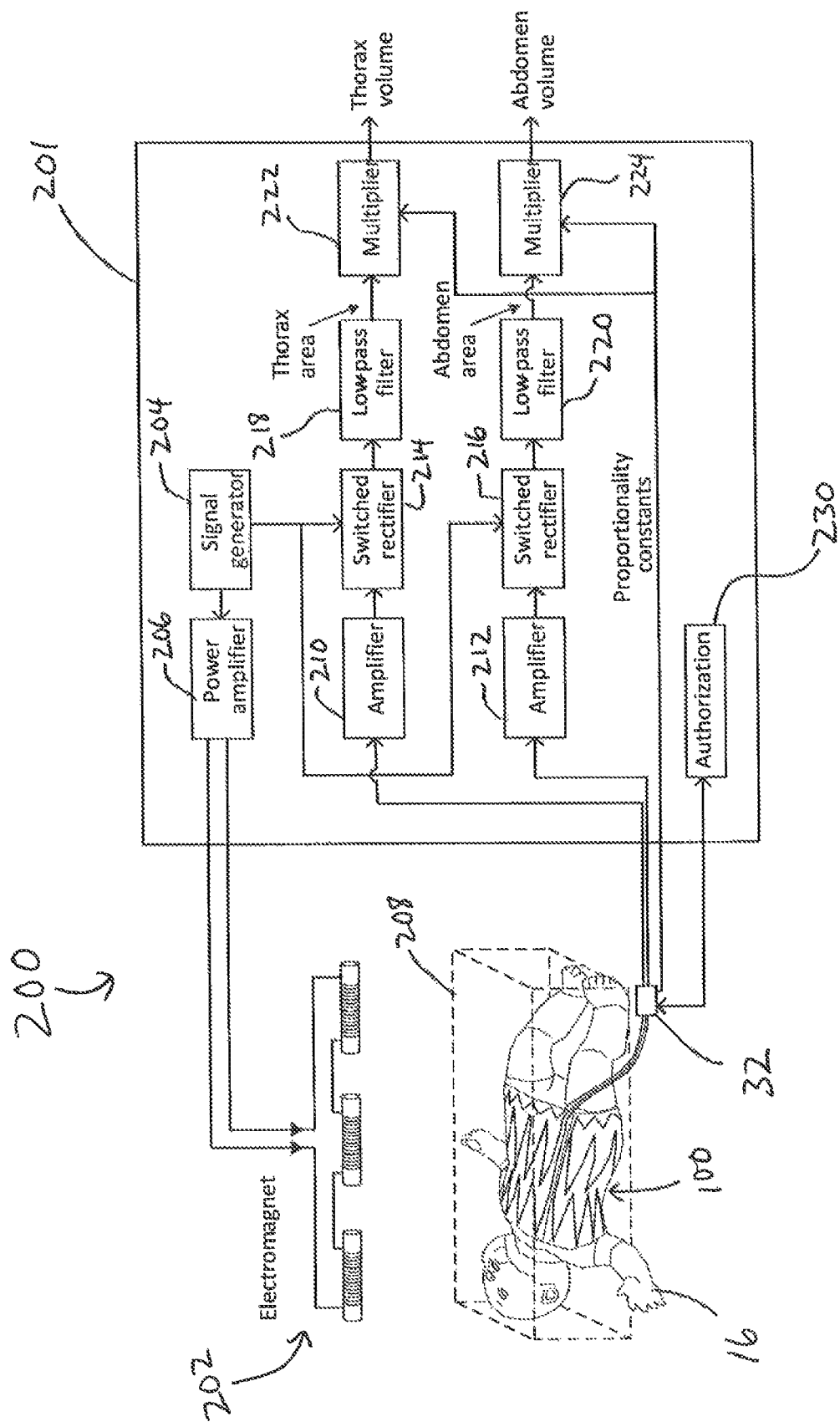
FIG. 11 is a schematic of a system for measuring a volume of a subject according to an embodiment of the invention.

FIG. 11 is a schematic of a system 200 for measuring one or more volumes of the subject 16 according to some embodiments of the invention. In general, the system 200 includes the coil device 100, a control system 201, and an electromagnet 202 for generating a relatively homogeneous magnetic field. Although the coil device 100 is depicted, a coil device according to any embodiment of the invention may similarly be used within the system 200.

The control system 200 may include a variety of elements similar in many respects to the systems described in U.S. Pat. Nos. 6,374,667; 6,945,941; and 7,390,307, which are hereby incorporated by reference herein in their respective entireties. For example, in some embodiments, the system integrates into a single system both the current source that powers the electromagnet 202 and the circuits needed to amplify and rectify the signals measured from the coil device 100. In some cases the components of the control system 200 may be implemented in hardware, firmware, and/or software depending upon the particular application and operating environment. For example, in some cases portions of the control system 200 may be implemented in hardware, such as on a dedicated circuit board, and other portions may be implemented in executable software instructions, either on the dedicated circuit board, or within a computer (e.g., a personal laptop computer) coupled with the dedicated board. Those skilled in the art will appreciate a variety of implementations other than these particular examples are possible.

The current source includes an alternating current signal generator 204 and power amplifier 206 that feed the electromagnet 202. The electromagnet 202 can take a variety of forms. For example, the electromagnet 202 can include one of the electromagnets described in U.S. Pat. Nos. 6,374,667; 6,945,941; and 7,390,307. Once energized, the electromagnet 202 generates a relatively homogeneous, time-varying field within a predefined spatial volume 208. For example, the field may have a coefficient of variation of less than five percent throughout the spatial volume 208. The electromagnet 202 is typically configured and positioned such that the predefined spatial volume 208 is positioned proximate to a subject support surface for measuring a volume of the subject 16 resting upon the support surface. For example, the electromagnet 202 may be positioned to generate the magnetic field within the spatial volume 208 proximate a crib, an incubator, a bed, or another suitable platform supporting the subject 16.

The signals induced in the members of the coil device 100 are fed into parallel processing paths in one embodiment. For example, as shown in FIG. 11, the signals are fed to corresponding amplifiers 210, 212, and then to corresponding switched rectifiers 214, 216. The gain of the amplifiers need not be more than necessary to suppress the noise of the rectifiers, with atypical value of about 20 to 25 dB. The switched rectifiers 214, 216 rectify the alternating voltage signals, and are easily implemented by CMOS analog switches. Upon being rectified, the signals are fed to corresponding low-pass filters 218, 220 for further processing.

In some embodiments, the signals exiting the low-pass filters 218, 220 generally correspond to the average cross-sectional areas of the first and second members of the coil device 100, respectively. The control system 200 may retrieve one or more proportionality constants stored in electronic memory associated with the coil device 100 (e.g., located within connector 32) and use these to estimate the volumes of the subject 16 in multipliers 222, 224. The multipliers 222, 224 may be implemented in hardware, firmware, and/or software depending upon the particular environment and operating environment. The resulting signals, in this case indicating a volume of the subject's chest (thorax) and abdomen, are then available for output or further processing if desired.

In some embodiments, the control system 200 further includes an authorization module 230 that may communicate with the optional electronic memory of the coil device 100. The authorization module 230 retrieves authorization data from the electronic memory and is adapted to determine whether use of the coil device 100 is authorized. For example, the authorization module 230 may compare a current count of authorized uses with a maximum count of authorized uses allowed for the coil device stored within the electronic memory. The authorization module 230 may further compare a subject identifier with a stored identifier to determine if use of the coil device 100 is authorized for a particular subject.

Of course, a variety of other elements can be included within the control system 200 to, e.g., further condition and process the signals measured in the coil device 100. Just a few examples include additional amplifying or filtering elements and means for subtracting out a substantial DC or constant component (corresponding to the total volume of the body inside the coils) in the signals so that only changes in volume are detected. The volume signal can also be processed to detect respiratory cycles, and determine the frequency of respiration, tidal volume and a range of variables used in clinical spirometry. In addition, the rate of air flow in and out of the lungs can be calculated by differentiating the volume signal as a function of time.

Figure 12:
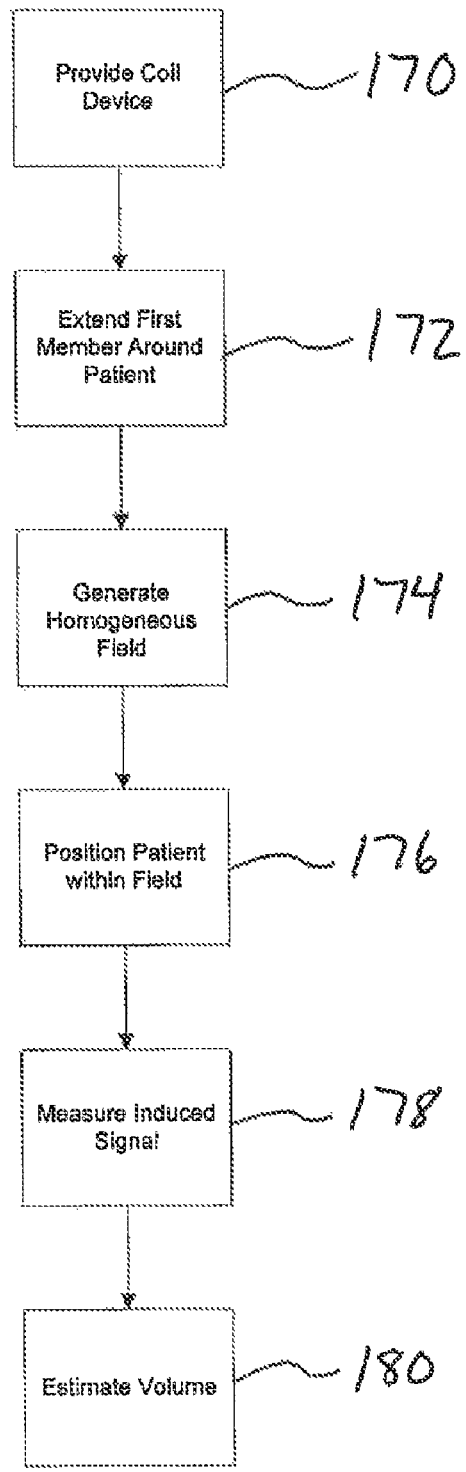
FIG. 12 is a flow diagram illustrating a method for measuring a volume of a subject according to an embodiment of the invention.

FIG. 12 is a flow diagram illustrating a method of measuring a volume of a subject. For example, the method may be useful for measuring a volume of a subject's abdomen and/or chest. In some cases the method includes providing (170) a coil device according to an embodiment of the invention, such as one of the coil devices 10, 100 described herein having at least a first member and a first conductor. The first member is then extended (172) around an outer surface of a first portion of the subject's abdomen and/or chest. In so doing, the first member is conformed to the outer surface despite changes in a contour of the outer surface. The first conductor is preferably extended only once around the subject's abdomen and/or chest.

Either before or after providing the coil device and extending it around the subject, the method includes generating (174) with an electromagnet a relatively homogeneous magnetic field throughout a predefined spatial volume. For example, an alternating current may be fed to an electromagnet to generate a time-varying, relatively homogeneous magnetic field throughout the spatial volume. In some cases this means that the magnetic field has a coefficient of variation throughout the spatial volume of less than five percent variation. After generating the field, the patient and coil device are positioned (176) within the magnetic field to induce a signal in the coil device. The induced signal is measured (178) by a connected control system, which can then estimate (180) a volume of the subject's abdomen and/or chest using the induced and measured signal.

In some embodiments, a second member having a second conductor may also be extended around an outer surface of a second portion of the subject's abdomen and/or chest. After positioning the second portion of the subject's abdomen and/or chest within the spatial volume and magnetic field, a signal induced in the second conductor can be measured and used to estimate a volume of the second portion. As indicated above, the coil device may be used to measure the volume of a variety of areas of the subject. In one case, the first portion is at least part of the subject's abdomen and not part of the subject's chest. Corresponding to this arrangement, the second portion may be at least part of the subject's chest and not part of the subject's abdomen.

As previously discussed with reference to the figures, in some cases the signal measured in the first and/or second conductors corresponds to an average cross-sectional area of the first and second portions of the subject, respectively. In some embodiments, methods of the invention further include estimating the volume of the first and/or second portions by multiplying the average cross-sectional area (as represented by the measured signals) by a proportionality constant, such as the width of the first or second members, as explained with reference to FIG. 6.

Figure 13:
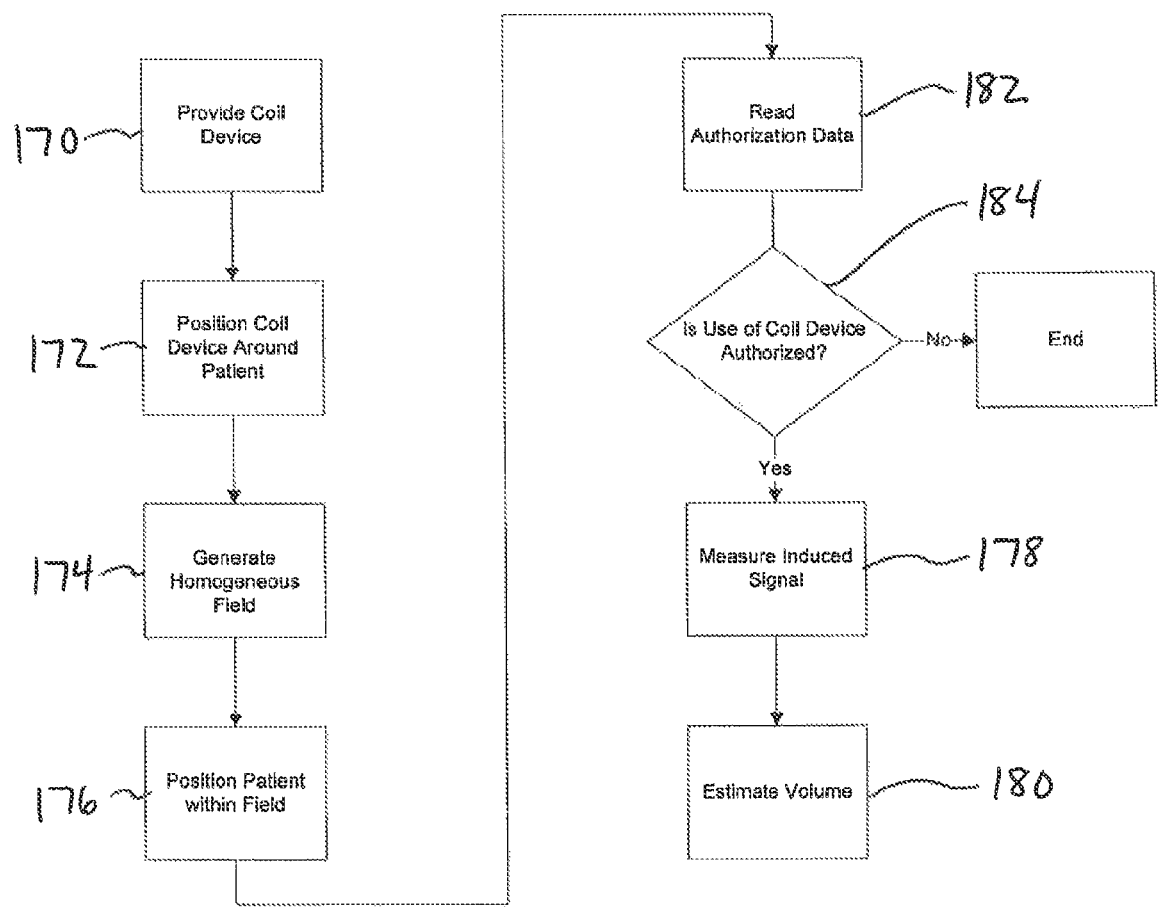
FIG. 13 is a flow diagram illustrating a method for authorizing the measurement of a volume of a subject according to an embodiment of the invention.

In some embodiments of the invention, the authorization data stored in the electronic memory 160 (see FIG. 10) can be used to secure the volume measuring process. For example, an operator may only be able to measure a volume of a subject if the authorization data indicates use of the particular patient coil device is authorized. Referring now to FIG. 13, some embodiments of the invention further provide for reading (182) the authorization data from the electronic memory and determining (184) from the authorization data whether use of the coil device is authorized. If use of the coil device is authorized, the method can further include measuring (178) the signals induced in the coil device and estimating (180) the volumes associated with those signals.

Of course, a number of variations related to the authorization data are possible. One or more steps in the process may be preconditioned upon authorization of the coil device. As just one example, in some cases the signal induced in the conductor(s) of the coil device may only be measured if use of the coil device is authorized.

In some embodiments, authorizing the coil device may include determining whether the coil device has exceeded a predetermined maximum number of authorized uses. For example, the authorization data may include a maximum count corresponding to the maximum number of authorized uses and a current count corresponding to an actual number of uses of the coil device. The current count can be compared with the maximum count to determine if the device is authorized for use. In further embodiments, the current count may be incremented after a use of the coil device by writing to the electronic memory to change the current count. This can allow the coil device to track the number of times it has been used.

In additional embodiments, a stored identifier within the electronic memory can associate a particular coil device with a particular subject. For example, a subject identifier can be assigned to the subject being monitored with the coil device and then stored in the electronic memory to associate the subject with the coil device. Upon later using the coil device, the device may first be authorized by comparing a subject identifier for the current subject with the stored identifier within the electronic memory. Use of the coil device may only be authorized if the two identifiers match.

Thus, embodiments of the Coil System And Method For Obtaining Volumetric Physiological Measurements are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. Apparatus for measuring volume, the apparatus comprising:
a substrate having a length, and a top and a bottom separated by a width, wherein the substrate is configured to extend, along the length of the substrate, around a portion of a subject;
a first conductor fastened to the substrate and extending only once along the length of the substrate, the first conductor occupying a first portion of the width of the substrate corresponding to a first portion of the subject, wherein the first conductor has a first end and a second end, and wherein the first end is electrically coupled to a first electrical lead that exits the substrate, the first conductor configured to provide via the first electrical lead a signal representative of a volume corresponding to the first portion of the subject; and
a second conductor fastened to the substrate and providing for the first conductor a return electrical path along the length of the substrate in a direction opposite to the first conductor, the second conductor extending only once along the length of the substrate and occupying a second portion of the width of the substrate, wherein the second conductor has a first end and a second end, the first end is electrically coupled to the second end of the first conductor, and the second end of the second conductor is electrically coupled to a second electrical lead that exits the substrate, the second conductor configured to generate a noise signal having an opposite polarity to a noise signal generated by the first conductor.

2. The apparatus of claim 1, further comprising:
a third conductor fastened to the substrate and extending only once along the length of the substrate, the third conductor occupying a third portion of the width of the substrate corresponding to a second portion of the subject, wherein the third conductor has a first end and a second end, the first end is electrically coupled to a third electrical lead that exits the substrate, and the third electrical lead is electrically separate from the first electrical lead, the third conductor configured to provide via the third electrical lead a signal representative of a volume corresponding to the second portion of the subject.

3. The apparatus of claim 2, wherein:
the substrate comprises a first free end on one side along its length, a second free end on an opposite side along its length, and a fastener for securing the first free end and the second free end together; and
the first electrical lead, the second electrical lead, and the third electrical lead all exit the substrate at a common area along the length of the substrate, thereby facilitating wrapping of the substrate around the subject and fastening of the first free end and the second free end together.

4. The apparatus of claim 2, wherein the second conductor provides for the first conductor and the third conductor a return electrical path along the length of the substrate in a direction opposite to the first conductor and the third conductor, wherein the first end of the second conductor is electrically coupled to the second end of the first conductor and to the second end of the third conductor, the third conductor configured to generate a noise signal having an opposite polarity to noise signals generated by the first conductor and the third conductor.

5. The apparatus of claim 4, wherein the substrate is configured such that the first portion of the width of the substrate corresponds to the subject's thorax.

6. The apparatus of claim 5, wherein the substrate is configured such that the third portion of the width of the substrate corresponds to the subject's abdomen.

7. The apparatus of claim 6, wherein the substrate is configured such that the second portion of the width of the substrate corresponds to the subject's hips.

8. The apparatus of claim 6, wherein the substrate is configured such that the second portion of the width of the substrate corresponds to a portion of the subject that does not change its volume during respiration of the subject.

9. The apparatus of claim 6, further comprising a control unit coupled to the first electrical lead, the second electrical lead, and the third electrical lead, and configured to detect when the subject's abdomen moves in asynchrony with the subject's thorax thereby indicating an asynchronous breathing pattern.

10. The apparatus of claim 4, wherein each of the first conductor and the third conductor extends in a triangularly-shaped, zigzag configuration along the length of the substrate.

11. The apparatus of claim 10, wherein the second conductor extends in a triangularly-shaped, zigzag configuration along the length of the substrate.

12. The apparatus of claim 4, wherein the first portion of the width of the substrate occupied by the first conductor is non-overlapping with the third portion of the width of the substrate occupied by the third conductor.

13. The apparatus of claim 12, wherein the second portion of the width of the substrate occupied by the second conductor is non-overlapping with the first portion of the width of the substrate occupied by the first conductor and the third portion of the width of the substrate occupied by the third conductor.

14. The apparatus of claim 4, Wherein at least one of the first conductor, the second conductor, and the third conductor is stamped or cut from a metal foil sheet.

15. The apparatus of claim 4, further comprising a connector coupled to the first electrical lead, the second electrical lead, and the third electrical lead, the connector comprising an electronic memory storing data for determining whether use of the substrate with the first, second, and third conductors is authorized.

16. The apparatus of claim 4, further comprising:
an electromagnet configured to generate a magnetic field in the vicinity of the substrate comprising the first conductor, the second conductor, and the third conductor in order to cause the first conductor to provide via the first electrical lead the signal representative of the volume corresponding to the first portion of the subject, the third conductor to provide via the third electrical lead the signal representative of the volume corresponding to the second portion of the subject, and the second conductor to generate the noise signal having the opposite polarity to noise signals generated by the first conductor and the third conductor; and a control system electrically coupled to the first electrical lead, the second electrical lead, and the third electrical lead.

17. The apparatus of claim 16, wherein the electromagnet is configured to generate a magnetic field having a coefficient of variation of less than 5%.

18. The apparatus of claim 16, wherein the control system comprises:
a first amplifier electrically coupled to the first electrical lead for amplifying the signal representative of the volume corresponding to the first portion of the subject; and
a second amplifier electrically coupled to the third electrical lead for amplifying the signal representative of the volume corresponding to the second portion of the subject.

19. The apparatus of claim 18, further comprising:
a first multiplier electrically coupled to the first amplifier and configured to multiply a signal output by the first amplifier by a first proportionality constant; and
a second multiplier electrically coupled to the second amplifier and configured to multiply a signal output by the second amplifier by a second proportionality constant.

20. The apparatus of claim 1, wherein the substrate comprises an elastic material that is configured to expand or retract in response to volumetric changes in the portion of the subject around which the substrate is placed.

21. The apparatus of claim 1, wherein the substrate is a continuous sleeve.

22. The apparatus of claim 1, wherein the substrate comprises a first end and a second end separated by the length, and wherein the substrate is configured to assume (i) an open position in which the first end and the second end of the substrate are not joined such that the portion of the subject around which the substrate is to be placed can pass between the first and second ends of the substrate, and (ii) a closed position in which the first end and the second end are joined and the substrate extends around the portion of the subject.

23. The apparatus of claim 22, wherein the substrate is rectangularly-shaped when in the open position.

24. The apparatus of claim 22, wherein the substrate is cylindrically-shaped when in the closed position.

* * * * *